United States Patent
Krijgsman et al.

(10) Patent No.: US 6,319,684 B1
(45) Date of Patent: Nov. 20, 2001

(54) PROCESS FOR THE FERMENTATIVE PRODUCTION OF CEPHALOSPORIN

(75) Inventors: John Krijgsman, Dordrecht; Jan Willem Hubert Smeets, Vlaardingen; Henriëtte Elisabeth Anna De Braal, Delft; Erik De Vroom; Herman Pieter Fasel, both of Leiden, all of (NL)

(73) Assignee: DMS N.V., Ma Delft (NL)

( * ) Notice: Subject to any disclaimer, the term of this patent is extended or adjusted under 35 U.S.C. 154(b) by 0 days.

(21) Appl. No.: 09/202,370

(22) PCT Filed: Apr. 22, 1998

(86) PCT No.: PCT/EP98/02459

§ 371 Date: Aug. 26, 1999

§ 102(e) Date: Aug. 26, 1999

(87) PCT Pub. No.: WO98/48036

PCT Pub. Date: Oct. 29, 1998

(30) Foreign Application Priority Data

Apr. 22, 1997 (EP) .................................................. 97201201

(51) Int. Cl.⁷ ........................................................ C12P 35/02
(52) U.S. Cl. .................................. 435/51; 435/47; 435/49; 435/50
(58) Field of Search ................................. 435/51, 49, 50, 435/47

(56) References Cited

U.S. PATENT DOCUMENTS 3,880,713 * 4/1975 Fleming et al. ......................... 435/51
5,559,005 * 9/1996 Conder et al. .......................... 435/47
5,731,165 * 3/1998 Bovenberg et al. .................... 435/47

FOREIGN PATENT DOCUMENTS

| 37 29 338 | 3/1989 | (DE) . |
| 0 532 341 | 3/1993 | (EP) . |
| 1 299 883 | 12/1962 | (FR) . |
| WO 93 08287 | 4/1993 | (WO) . |
| WO 95 04148 | 2/1995 | (WO) . |

OTHER PUBLICATIONS

International Search Report dated Aug. 26, 1998 for WO 98/48036.

* cited by examiner

*Primary Examiner*—Francisco Prats
(74) *Attorney, Agent, or Firm*—Morrison & Foerster LLP

(57) ABSTRACT

The present invention relates to a novel process for the preparation of cephalosporins having been deacylated at the 7-amino group, by fermentation of a cephalosporin producing microorganism in the presence of a side chain precursor, extraction of the N-substituted cephalosporin compound as present in the fermentation broth or fluid to an organic solvent, back extraction of the N-substituted cephalosporin compound to water, treatment of the aqueous phase with a dicarboxylate acylase and isolation of the crystalline cephalosporin compound according to formula (1) from the conversion solution, characterized in that the fermentation broth or fluid is incubated at acidic conditions and an elevated temperature prior to extraction of the N-substituted cephalosporin compound to an organic solvent. Further improvements of the process are obtained by washing the first organic solvent extract with acidified water and/or by extraction of the side chain to an organic solvent and/or by treating an aqueous cephalosporin solution produced at one or more stages in the process of the invention with carbon dioxide.

12 Claims, No Drawings

PROCESS FOR THE FERMENTATIVE
PRODUCTION OF CEPHALOSPORIN

FIELD AND BACKGROUND OF THE
INVENTION

The present invention relates to the recovery of fermentatively produced cephalosporin compounds.

Semi-synthetic routes to prepare cephalosporins mostly start from fermentation products such as penicillin G, penicillin V and Cephalosporin C, which are converted to the corresponding β-lactam nuclei, for instance in a manner as is disclosed in K. Matsumoto, Bioprocess. Tech., 16, (1993), 67–88, J. G. Schewale & H. Sivaraman, Process Biotechnology of August 1989, 146–154, T. A. Savidge, Industrial Antibiotics (Ed. E. J. Vandamme) Marcel Dekker, N.Y., 1984, or J. G. Shewale et al., Process Biochemistry International, June 1990, 97–103. The obtained β-lactam nuclei are subsequently converted to the desired antibiotic by coupling to a suitable side chain, as has been described in inter alia EP 0 339 751, JP-A-53005185 and CH-A-640 240. By making different combinations of side chains and β-lactam nuclei, a variety of penicillin and cephalosporin antibiotics may be obtained.

7-Amino desacetoxy cephalosporanic acid (7-ADCA) and 7-amino cephalosporanic acid (7-ACA) are know to be the most important intermediates for the production of antibiotics used in the pharmaceutical industry.

7-ADCA is for example obtained by chemical or enzymatic cleavage (deacylation) of phenlacetyl-7-ADCA yielding 7-ADCA and phenylacetic acid. Phenylacetyl-7-ADCA yielding 7-ADCA by chemical treatment of penicillin G sulfoxide, which is formed from penicillin G. In this production process a large amount of chemicals are required to ensure that the desired reaction takes place. This is both expensive and places a heavy burden on waste management. Moreover, the total yield of the process is not as high as would be desired.

To overcome some of the drawbacks of the chemical process a fermentative process has been disclosed for the production of 7-ADCA and 7-ACA, involving fermentative production of N-substituted β-lactams, such as adipyl-7-ADCA or adipyl-7-ACA, by a recombinant *Penicillin chrysogenum* strain capable of expressing a desacetoxycephalosporanic acid synthase (DAOCS) also know as "expandase" from a transgene (EP 0 532 341, EP 0 540 210, WO 93/08282, WO 95/04148, WO 95/04149). The expandase takes care of the expansion of the 5-membered ring of certain N-acylatec penicillanic acids, thereby yielding the corresponding N-acylated desacetoxycephalosporanic acids.

Known processes for recovering chemically or enzymatically produced penicillanic and cephalosporanic acids acids are not effective for the recovery of the N-substituted β-lactam intermediates and deacylated amino- β-lactams. The main problem with the recovery of the fermentatively produced N-substituted cephalosporin compounds mentioned hereinabove is the complexity of the broth, or culture filtrate. The broth usually comprises various penicillanic acids, such as α-aminoadipyl-6-penicillanic acid, α-hydroxyadipyl-6-penicillanic acid, 6-aminopenicillanic acid (6-APA), various cephalosporanic acids including α-aminoadipyl- and α-hydroxyadipyl-7-ADCA and a lot of proteinaceous material. Known recovery procedures do not give an acceptable quality of the cephalosporanic acid product in terms of purity.

In the enzymatic deacylation this leads to problems in terms of reduced enzyme half-life, slower bioconversion rate and more expenses in the recovery after bioconversion and/or unacceptable contaminant levels. Moreover, after deacylation, such impurities prevent or at least hamper the recovery of the desired deacylated cephalosporin compound with the desired specifications.

Therefore the known procedures penicillins and cephalosporins do not give an acceptable quality of end product: the end product, e.g. 7-ADCA or 7-ACA, contains an unacceptable amount of penicillin components as impurities.

DESCRIPTION OF THE INVENTION

The present invention relates to an improved process for the production of deacylated β-lactams, for instance 7-ADCA or 7-ACA, from a fermentation broth of a cephalosporin producing microorganism.

In particular, the present invention discloses an improved process for the preparation of cephalosporins having been deacylated at the 7-amino group and having the general formula I

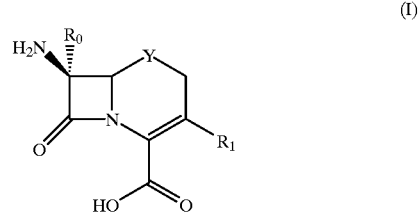

wherein: $R_0$ is hydrogen or $C_{1-3}$ alkoxy;
Y is $CH_2$, oxygen, sulfur, or an oxidized form of sulfur; and
$R_1$ is any of the groups selected from hydrogen, hydroxy, halogen, $C_{1-3}$ alkoxy, optionally substituted, optionally containing one or more heteroatoms, saturated or unsaturated, branched or straight $C_{1-5}$ alkyl, preferably methyl, optionally substituted, optionally containing one or more heteroatoms $C_{5-8}$ cycloalky, optionally substituted aryl or heteroaryl, or optionally substituted benzyl, by fermentation of a cephalosporin producing microorganism in the presence of a side chain precursor, extraction of the N-substituted cephalosporin compound as present in the fermentation broth or fluid to an organic solvent, back extraction of the N-substituted cephalosporin compound to water, treatment of the aqueous phase with a dicarboxylate acylase and isolation of the crystalline cephalosporin compound according to formula 1 from the aqueous phase, characterized in that the fermentation broth or fluid or the back extract is incubated at acidic conditions and an elevated temperature prior to extraction of the fermentation broth or fluid with an organic solvent or prior to further processing of the back extract.

Additional improvements of the process are obtained by washing the first organic solvent extract containing the N-substituted cephalosporin compound with acidified water and/or by treating aqueous cephalosporin solutions produced at one or more stages in the process of the invention with carbon dioxide and/or by extracting the enzymatically released side chain to an organic solvent prior to crystallization of the deacylated cephalosporin.

The process according to the invention will give a better overall yield and product quality than the currently known processes.

In the novel recovery processes, applied to obtain a deacylated cephalosporin compound from its N-acylated counterpart, e.g. 7-ADCA from adipyl-7-ADCA or 7-ACA from adipyl-7-ACA, the following steps are described in more detail.

A fermentation broth is obtained from any suitable fermentation process, e.g. from a fermentation using a strain of *Penicillium chrysogenum* in the presence of a suitable side chain precursor, as mentioned hereinabove.

The biomass is separated from the fermentation broth using any suitable technology, such as centrifugation or filtration, yielding a cephalosporin-containing fermentation fluid. Preferably, a filtration step is applied to obtain said separation. The residual solids optionally are washed.

One of the obstacles of producing N-substituted cephalosporanic acid is the presence of unwanted contaminating β-lactam components, especially 6-amino penicillanic acid (6-APA), N-substituted 6-APA or α-aminoadipyl-7-ADCA.

In a preferred embodiment of the invention, contaminations are remarkably reduced by incubating an aqueous solution containing the N-substituted cephalosporin compound produced at any stage in the process of the invention under acidic conditions and an elevated temperature. The aqueous solution containing the N-substituted cephalosporin compound is acidified to a pH which is lower that 4, preferably lower than 3, using one or more known acids, for instance sulfuric acid, hydrochloric acid or nitric acid or a combination thereof. The operation temperature is in the range of 20 to 140° C., preferably at 60 to 80° C. The residence time at these conditions is in the range of several days to several minutes, preferably less than 60 minutes, more preferably 1 to 30 min.

The above incubation step according to the invention can be applied to the fermentation broth or fluid or to the N-substituted cephalosporin-containing aqueous back extract. Preferably the incubation step is applied to the fermentation broth or fluid. The incubation step can further be carried out either before or after separation of the biomass. Preferably, the incubation is carried out before filtration, to have an advantage in filtration.

The N-substituted cephalosporin compound is separated from the aqueous phase, i.e. the fermentation broth or fluid, by means of acidification of the fermentation broth or fluid and subsequent extraction of the N-substituted cephalosporin compound to an organic solvent. Acidification typically occurs to a pH lower than 4, preferably lower than 3, and only in the case that the fermentation broth or fluid is not yet subjected to the above mentioned incubation under acidic conditions and an elevated temperature. A suitable de-emulsifier may be added to the fermentation broth or fluid to improve the extraction significantly.

Preferably, the organic solvent is selected from the group of amyl acetate, butyl acetate, ethyl acetate, methyl isobutyl ketone, cyclohexanone, iso-butanol or n-butanol.

The extraction with an organic solvent as described above has no satisfactory selectivity towards the unwanted β-lactam products such as α-aminoadipyl-7-ADCA and 6-APA. Therefore, in a preferred embodiment of the invention a wash process is performed for specific removal of these compounds. The wash process is characterized by mixing the organic solvent-extract with a small amount of acidified water, followed by phase separation. The acidified water typically has a pH which is lower than 4, preferably lower that 3, more preferably lower than 2. In addition, the phase ratio typically is in between 1:1 to 1:20 water:solvent, preferably 1:2 water:solvent.

The N-substituted cephalosporin compound is back extracted to water in conventional ways by extracting the organic phase with an alkaline solution, to yield an aqueous back extract with a pH within the range of 6 to 9. Typically, a phase ratio of 1:10 (water:solvent) is applied. The alkaline solution is an aqueous solution containing a conventional mineral base, such as NaOH or $NH_3$.

Extraction, washing and back extraction are preferably performed in a series of continuous intensive contact extractors, for instance a combination of an intense mixer, for instance a high shear mixer, with a centrifugal separation, preferably 2 to 8, more preferably 3 to 6 and most preferably 4 to 5.

After phase separation, the aqueous phase optionally is stripped to remove the solvent.

Subsequently, the aqueous solution is contacted with a suitable dicarboxylate acylase enzyme, to deacylate the N-substituted cephalosporin compound. For instance, to form 7-ADCA or 7-ACA from the corresponding N-adipyl derivatives.

Organisms that have been found to produce dicarboxylate acylase are Alcaligens, Arthrobacter, Achromobacter, Aspergillus, Acinetobacter, Bacillus and Pseudomonas species. More in particular, the following species produce highly suitable dicarboxylate acylases: *Achromobcter xylosooxidans, Arthorobacter viscosis, Arthrobacter* CA128, *Bacillus* CA78, *Bacillus megaterium* ATCC53667, *Bacillus cereus, Bacillus laterosporus* J1, *Paecilomyces* C2106, *Pseudomonas diminuta* sp N176, *Pseudomonas diminuta* sp V22, *Pseudomonas paucinobilis, Pseudomonas diminuta* BL072, *Pseudomonas* strain C427, *Pseudomonas* sp SE83, *Pseudomonas* sp SE495, *Pseudomonas ovalis* ATCC950, *Comamonas* sp SY77, *Pseudomonas* GK 16, *Pseudomonas* SY-77-1, *Pseudomonas* sp A14, *Pseudomonas vesicularis* B965, *Pseudomonas syringae, Ps putida* ACTCC17390, *Ps aeroginosa* NCTC 101701, *Proteus vulgaris* ACTCC9634, *Ps fragi* DSM3881, and *B. subtilus* IFO3025.

The dicarboxylate acylase may be obtained from the microorganism by which it is produced in any suitable manner, for example as is described for the Pseudomonas sp SE83 strain in U.S. Pat. No. 4,774,179. Also, the genes for the e.g. SE83 or SY77 dicarboxylate acylases may be expressed in a different suitable host, such as *E. coli* as has been reported by Matsuda et al. in J. Bacteriology, 169, (1987), 5818–5820 for the SE83 strain, and in U.S. Pat. No 5,457,032 for the SY77 strain.

The enzymes isolated from the above sources are often referred to as glutaryl acylases. However, the side chain specificity of the enzymes in not limited to the glutaryl side chain, but comprises also smaller and larger dicarboxyl side chains. Some of the dicarboxylate acylases also express gamma-glutamyl transpeptidase activity and are therefore sometimes classified as gamma-glutamyl transpeptidases.

The dicarboxylate acylase may be used as the free enzyme, but also in any suitable immobilized form, for instance as has been described in EP 0 222 462.

In one embodiment of the invention, the deacylated cephalosporin compound, e.g. 7-ADCA or 7-ACA, is isolated from the conversion solution by crystallization at acidic conditions. Typically, crystallization of a deacylated cephalosporin compound from an aqueous solution is performed by adjusting the pH of the aqueous solution to an acidic value by adding a titrant to the aqueous solution until the pH has reached a value within a range of 2.5–4.5, preferably a value of 3–4.

In a preferred embodiment of the invention, crystallization of a deacylated cephalosporin compound from an aqueous solution is carried out by adding the aqueous solution to a crystallization vessel which is kept at a fixed pH having a value within a range of 2.5–4.5, using a suitable titrant.

In an even more preferred embodiment of the invention, said crystallization is carried out by a stepwise adjustment of the pH of the aqueous solution to a final value within a range of 2.5–4.5 by adding the aqueous solution to a series of interconnected crystallization vessels, i.e. adding the aqueous solution to a first vessel, simultaneously adding the content of the first vessel to a second vessel, simultaneously adding the content of the second vessel to a third vessel, etc., wherein a pH range is applied in the interconnected vessels using a suitable titrant, starting at a pH in the first vessel which deviates about 0.5–2 pH units from the pH of the aqueous solution containing the deacylated cephalosporin end ending at at pH in the final vessel which has a value within a range of 2.5–4.5. Conveniently, the pH of the aqueous solution containing the deacylated cephalosporin is adjusted to the desired final value using a series of 2–6 interconnected vessels.

For instance, to obtain crystallization of a deacylated cephalosporing from the conversion solution, a decreasing pH range from 8 to 3 can be applied using a titrant which is an acid, such as sulfuric acid, hydrochloric acid and/or nitric acid, applying a series of 3–4 interconnected vessels.

The two preferred embodiments described above are preferably performed in a continuous mode.

In a further preferred embodiment of the invention, the side chain, coloured products and traces of unconverted compound are removed from the conversion solution prior to crystallization following the steps as indicated hereinbelow.

The conversion solution is acidified and contacted with an organic solvent, for instance amyl acetate, butyl acetate, ethyl acetate, methyl isobutyl ketone, cyclohexanone, isobutanol or n-butanol, to remove the side chain prior to crystallization. The acidification is performed with an acid, such as sulfuric acid, hydrochloric acid or nitric acid or a combination thereof, preferably sulfuric acid, to a pH lower that 3, preferably lower than 2. Unexpectedly, also a high removal efficiency of the coloured impurities is obtained in addition to that of the side chain.

According to another preferred embodiment of the invention, contaminating penicillin components, for instance zwitterionic 6-APA, as present in the aqueous cephalosporin-containing solutions produced at one or more stages of the process of the invention, such as the fermentation broth or fluid, the back extract, the conversion solution, or the solution containing the dissolved deacylated cephalosporin according to formula (I), are remarkably reduced by contacting the penicillin-contaminated fluid, typically at pH 5 to 7, with carbon dioxide. Carbon dioxide can be added to the solution in any suitable way, such as in a solid or gaseous form or as a solution of a carbonate ions. The aqueous cephalosporin-containing solution is contacted with the $CO_2$ source at a temperature of 10 to 60° C., preferably 20 to 40° C., where said solution is saturated with molecular $CO_2$ for 4 to 10 hours. After reduction of the penicillin components, purification of the cephalosporin compounds according to formula (I) can be obtained.

After extraction of the side chain to an organic solvent, the deacylated cephalosporin compound can be crystallized from the aqueous phase in several ways, such as the ways which are indicated hereinabove for crystallization of a deacylated cephalosporin compound from an aqueous solution.

In a preferred mode of operation, the pH of the aqueous phase is increased to a pH having a value within a range of 2.5–5, preferably within a range of 3.5–4.5, by adding the solution containing the deacylated cephalosporin compound in one step to a crystallization vessel kept at the desired pH value or to a series of 2–6 interconnected crystallization vessels applying an increasing pH range. These processes can conveniently be carried out in continuous mode.

The crystals are isolated by filtration or centrifugation and dried in a conventional continuous or batch dryer.

All of the above mentioned steps, i.e. extraction, wash, back extraction and crystallization, can be carried out in batch or fed batch mode, but because of stability reasons, the preferred method is a continuous mode.

The following example is to exemplify only and should not be regarded to be a limitation whatsoever.

EXAMPLE

A sample of 1 l of adipyl-7-ADCA broth was filtrated to remove the biomass. The mycelium was washed with tap water to obtain a final volume of the filtrate of about 2 l.

Circa 2 l of filtrate was acidified at 40° C. with 250 ml of 6N $H_2SO_4$ to pH 1.5. N-butanol was added at ⅔ of the volume of the acidified filtrate and after vigorous mixing, separated. The waterphase was subjected to 2 more of these treatments with n-butanol. Subsequently the combined organic phases were washed with portions of 0.25 l of acidified water having a pH of 2. The resulting organic phase was back extracted with 245 ml of 2N NaOH solution at 20° C. and after phase separation the traces of n-butanol in the waterphase were removed by stripping under vacuum.

135 g of waterphase was diluted with demineralized water to a total of 650 ml at 30° C. and was mixed with 4N NaOH until pH 8.5. 50 g of immobilized deacylation enzyme was added and after 2 h at 30° C., pH 8.5, under addition of 13.5 ml of 4N NaOH the waterphase was collected. The filtrate was extracted with 3 portions of 125 ml of water saturated n-butanol at a pH of 0.4. During the extraction in total 50.6 ml of 37% HCl was added. The remaining waterphase was neutralized with 56.5 ml of 8N NaOH and the product was crystallized from the waterphase, free from n-butanol droplets, by lowering the pH to 5.3 with 6N $H_2SO_4$. After 5 minutes the pH was decreased further to the final value of 3.5. In total 15 ml of acid were used. The slurry was filtered and the crystal cake was washed with 50 of water, the cake was dried and 4.1 g of 96% pure 7-ADCA was obtained.

What is claimed is:

1. A process for preparing a cephalosporin of the formula

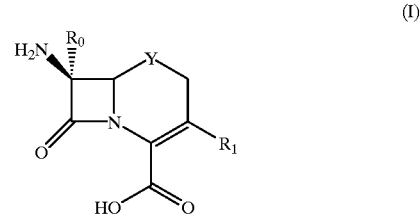

(I)

wherein $R_0$ is hydrogen or $C_{1-3}$ alkoxy;

Y is $CH_2$, O, S or an oxidized form of S; and $R_1$ is selected from the group consisting of H, OH, halogen, $C_{1-3}$ alkoxy, $C_{1-5}$ alkyl which is saturated or unsaturated, branched or straight, said alkyl being optionally substituted and optionally containing one ore more heteroatoms, $C_{5-8}$ cycloalkyl, said cycloalkyl being optionally substituted and optionally containing one or more heteroatoms, optionally substituted aryl, optionally substituted in heteroaryl, and optionally substituted benzyl;

which comprises (a) extracting an N-substituted cephalosporin into an organic solvent from a fermentation broth of a cephalosporin producing microorganism, said fermentation having been conducted in the presence of a dicarboxylic acid cephalosporin N-side chain precursor, to obtain an organic solvent extract containing the N-substituted cephalosporin:

(b) back-extracting the N-substituted cephalosporin into an aqueous phase, thus obtaining an aqueous phase containing said N-substituted cephalosporing and (c) treating said aqueous phase containing N-substituted cephalosporin with a dicarboxylate acylase to convert said N-substituted cephalosporin into the compound of formula (I); and (d) optionally isolating said compound of formula (I) by crystallization;

wherein the fermentation broth extracted in step (a) or the aqueous phase containing N-substituted cephalosporin or the compound formula (I) in step (c) is incubated at a pH lower than 4 and a temperature of 60° C. or higher.

2. The process of claim 1, wherein said pH is lower than 3.

3. The process of claim 1, wherein said temperature is within a range of 60 to 80° C.

4. The process of claim 1, wherein said incubating is for a time less than 60 minutes.

5. The process of claim 1, comprising the further step, prior to step (b), of washing the organic solvent extract containing the N-substituted cephalosporin obtained in step (a) with acidified water having a pH lower than 4.

6. The process of claim 5, wherein said water has a pH lower than 3.

7. A process of claim 6, wherein said water has a pH lower than 2.

8. The process of claim 1, comprising the further step of extracting the compound of formula I into an organic solvent prior to step (d).

9. The process of claim 1, wherein the fermentation broth or the aqueous phase of step (c) is contacted with carbon dioxide.

10. The process of claim 9, wherein carbon dioxide is in a solid or gaseous form or as a solution of carbonate ions.

11. The process of claim 1, wherein the organic solvent is selected from the group consisting of amyl acetate, butyl acetate, ethyl acetate, methyl isobutyl ketone, cyclohexanone, iso-butanol and n-butanol.

12. The process of claim 1, wherein step (d) is performed by adding the aqueous phase of (c) to a crystalline vessel which is kept at a fixed pH having a value within a range of 2.5–4.5, using a suitable titrant.

* * * * *

UNITED STATES PATENT AND TRADEMARK OFFICE
CERTIFICATE OF CORRECTION

PATENT NO.    : 6,319,684 B1
DATED         : November 20, 2001
INVENTOR(S)   : John Krijgsman et al.

It is certified that error appears in the above-identified patent and that said Letters Patent is hereby corrected as shown below:

<u>Title page,</u>
Item [73], Assignee, delete "DMS N.V., Ma Delft (NL)" and insert -- DSM N.V., Ma Delft (NL) --.

Signed and Sealed this

Tenth Day of December, 2002

JAMES E. ROGAN
*Director of the United States Patent and Trademark Office*